US008679409B2

(12) United States Patent
Zhang et al.

(10) Patent No.: US 8,679,409 B2
(45) Date of Patent: Mar. 25, 2014

(54) FILTER DEVICE, FILTER METHOD AND TRACE DETECTOR

(75) Inventors: Yangtian Zhang, Beijing (CN); Jin Lin, Beijing (CN)

(73) Assignee: Nuctech Company Limited, Beijing (CN)

( * ) Notice: Subject to any disclaimer, the term of this patent is extended or adjusted under 35 U.S.C. 154(b) by 600 days.

(21) Appl. No.: 12/994,231

(22) PCT Filed: Jun. 25, 2010

(86) PCT No.: PCT/CN2010/074487
§ 371 (c)(1),
(2), (4) Date: Nov. 23, 2010

(87) PCT Pub. No.: WO2011/075992
PCT Pub. Date: Jun. 30, 2011

(65) Prior Publication Data

US 2012/0012743 A1 Jan. 19, 2012

(30) Foreign Application Priority Data

Dec. 24, 2009 (CN) .......................... 2009 1 0243773

(51) Int. Cl.

| | |
|---|---|
| ***A61L 2/00*** | (2006.01) |
| ***G01N 30/96*** | (2006.01) |
| ***A62B 7/08*** | (2006.01) |
| ***B01J 19/08*** | (2006.01) |
| ***B03C 3/68*** | (2006.01) |
| ***B03C 3/74*** | (2006.01) |

(52) U.S. Cl.
USPC ..... 422/121; 422/22; 422/186.1; 422/186.04; 422/186.15; 96/55; 96/57; 96/63; 96/66; 96/25; 96/75; 73/23

(58) Field of Classification Search
USPC ............... 422/22, 50, 88, 121, 186.1, 186.04, 422/186.15; 96/55, 57, 63, 66, 25, 18; 95/75; 73/23
See application file for complete search history.

(56) References Cited

U.S. PATENT DOCUMENTS 4,261,698 A * 4/1981 Carr et al. ..................... 436/138
5,024,685 A 6/1991 Torok et al.

(Continued)

FOREIGN PATENT DOCUMENTS

| | | |
|---|---|---|
| CN | 1184781 A | 6/1998 |
| JP | 5-200323 | 8/1993 |
| WO | 2006129101 | 12/2006 |
| WO | WO 2007/053028 | 5/2007 |
| WO | 2009075674 | 6/2009 |

OTHER PUBLICATIONS

Search Report and Written Opinion from corresponding Patent Application Serial No. PCT/CN2010/074487, dated Oct. 21, 2010.

(Continued)

*Primary Examiner* — Monzer R Chorbaji
(74) *Attorney, Agent, or Firm* — Westman, Champlin & Koehler, P.A.

(57) ABSTRACT

The present invention discloses a filter device. The filter device comprises a housing with an air inlet and an filtered air outlet; a high voltage electric field region provided between two ends of the housing, wherein the direction of the electric field is perpendicular to the direction along which the air is introduced into the housing; an ionization source provided in the electric field region to ionize the ionizable pollutants present in the air introduced from the air inlet and form the resultant ionized pollutants which will move towards both ends of the housing under the influence of the electric field; and a discharging device for discharging the ionized pollutants which have arrived at the ends of the housing out of the filter device. The present invention also relates to a filtering method of using the filter device, and a trace detector. The filter device can be used to ionize the ionizable interferents existed in the air, separate the ionized interferents from the other components of the air under the influence of the electric field, and discharge the interferent out of the filter device, thereby reducing the consumption of the consumables or even eliminating the need for consumables. The filter device in accordance with the present invention is applicable to a trace detector based on ion mobility technology for the detection of trace amounts of substances.

8 Claims, 1 Drawing Sheet

(56) References Cited

U.S. PATENT DOCUMENTS

| | | | | |
|---|---|---|---|---|
| 5,466,279 | A | 11/1995 | Hattori et al. | 96/69 |
| 5,656,063 | A * | 8/1997 | Hsu | 95/58 |
| 6,964,189 | B2 * | 11/2005 | Carlson et al. | 73/28.02 |
| 7,306,655 | B2 | 12/2007 | Kiern et al. | 96/83 |
| 2005/0193803 | A1 | 9/2005 | Carlson et al. | |
| 2007/0145166 | A1 | 6/2007 | Loreth | |
| 2007/0163327 | A1 | 7/2007 | Mansson | 73/31.02 |
| 2007/0266855 | A1 * | 11/2007 | Fleisher | 96/16 |
| 2009/0166532 | A1 | 7/2009 | Hu et al. | |

OTHER PUBLICATIONS

Corrected Written Opinion of International Search Authority from corresponding Patent Application Serial No. PCT/CN2010/074-487, dated Oct. 21, 2010; 5 pages.

First Office Action (in Chinese) for Chinese Application No. 200910243773.1, issued May 28, 2012, 4 pages.

Communication dated Jun. 3, 2013 with the extended European Search Report for Appln. No. 10779199.8-1803/2517795.

* cited by examiner

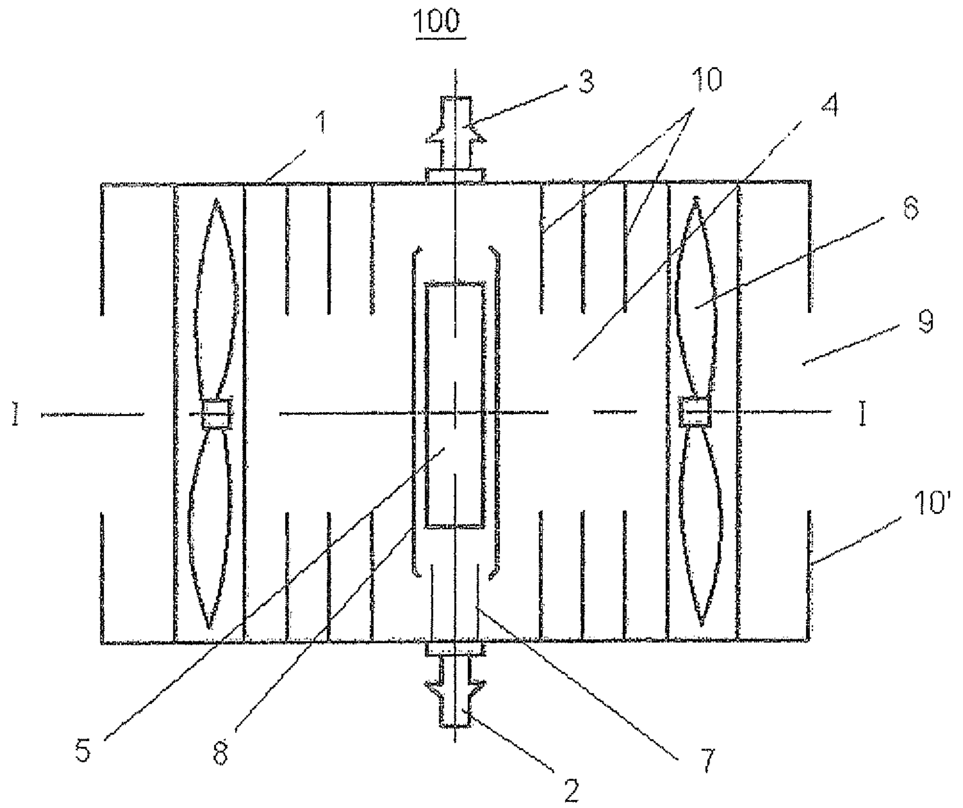
100
3
10
4
1
6
9
I
I
10'
5
8
2
7

FILTER DEVICE, FILTER METHOD AND TRACE DETECTOR

CROSS-REFERENCE TO RELATED APPLICATION

This Application is a Section 371 National Stage Application of International Application No. PCT/CN2010/074487, filed Jun. 25, 2010 and not yet published, the contents of which are hereby incorporated by reference in their entirety.

FIELD OF THE INVENTION

The present invention relates to a filter device which is applicable to a trace detector or other instruments where air is filtered. The invention further relates to a filter method of using the filter device and a trace detector.

BACKGROUND OF THE INVENTION

Conventionally, a filter material storage device is arranged in the gas passage system for filtering. But the filter material itself will gradually become ineffective during the filtration of air and needs to be treated before reuse, or removed and replaced with new filter material. Thus, the filter material is used as a consumable, a large consumption of which will thereby lead to not only an increase in the cost but inconvenience for users during operation and maintenance.

To solve the above problems, some compromising solutions are provided, such as a method of using a filter material that can be regenerated automatically, wherein a reusable filter material is used and in case of getting ineffective, cleaned by thermal treatment within the instrument and reused after the recovery of its function without the need for replacement. The benefits of these methods reside in their capability to avoid replacing the filter material, however, a complicated gas passage system is usually necessary, and the power consumption for heating is relatively high.

SUMMARY OF THE INVENTION

The present invention aims to overcome at least one aspect of the disadvantages and defects existing in the prior art. Accordingly, an objective of the present invention is to provide a new filter device which can be used to decrease the consumption rate of the consumable or even avoid the use of the consumable in addition to achieving filtration effects.

According to one aspect of the present invention, there is provided a filter device, comprising: a housing with an air inlet and an filtered air outlet; a high voltage electric field region provided between two ends of the housing, wherein the direction of the electric field being perpendicular to the direction along which the air is introduced into the housing; an ionization source provided in the electric field region to ionize the ionizable pollutants present in the air introduced from the air inlet and form the resultant ionized pollutants which will move towards both ends of the housing under the influence of the electric field; and a discharging device for discharging the ionized pollutants which have arrived at the ends of the housing out of the filter device. With the use of the discharging device, the pollutants which have moved to the two ends of the housing can be basically prevented from diffusing back into the middle portion of the housing.

Preferably, the filter device further comprises an air guiding element for guiding the air to flow from the inlet through the ionization source. The filter device further comprises flow confining gratings encompassing the ionization source.

Preferably, the discharging device comprises a pair of fans provided in the vicinity of the two ends of the housing, respectively, and discharging channels arranged at an outer side of the pair of fans. As an alternative, the discharging device includes a pair of air pumps provided in the vicinity of the two ends of the housing respectively.

Preferably, the filter device further comprises a controller for adjusting the negative pressure in the inner portion of said housing by controlling the discharging device.

According to another aspect of the present invention, there is provided a filtering method for a filter device, wherein the filter device comprises a housing with an air inlet and a filtered air outlet; the method includes the following steps: providing a high voltage electric field region between two ends of the housing, wherein the direction of the electric field being perpendicular to a direction along which the air is introduced into the housing, providing an ionization source in the high voltage electric field region, providing a discharging device for discharging the ionized pollutants that have moved to the ends of the housing out of the filter device, and guiding the air to flow from the inlet through the ionization source. With the use of the discharging device, the pollutants which have moved to the two ends of the housing can be basically prevented from diffusing back into the middle portion of the housing.

In accordance with the description of the present invention, the interferents present in the air are partially ionized by means of an ionization method; then the ionized interferents are separated from the other components in the air under the influence of the electric field, move towards the two ends of the housing, and are discharged out of the filter device with the use of devices such as fans or the like. Since only a small amount of consumables or even no consumables are required to partially remove the ionizable pollutants, the above process in accordance with the present invention can be used to cut the cost for consumables, or even eliminate the need for consumables of the whole instrument. The filter device in accordance with the present invention is applicable to a trace detector based on ion mobility spectrometry for the detection of trace amount of substances.

BRIEF DESCRIPTION OF THE DRAWINGS

These and/or other aspects and advantages of this invention will be apparent and can be easily understood upon reference to the following description of the preferred embodiments in conjunction with the accompanying drawings, in which:

FIG. 1 shows a schematic view of a filter device according to an embodiment of the present invention.

DETAILED DESCRIPTION OF THE EMBODIMENTS

The technical methodology in accordance with the present invention will be further explained in detail below with reference to specific embodiments in conjunction with the accompanying drawings. The disclosure provided is an exemplification of the overall structure design of the invention but is not intended to limit the invention to the particular embodiments described herein.

Referring to FIG. 1, the filter device 100 comprises a housing 1 having an air inlet 2 and an filtered air outlet; a high voltage electric field region 4 provided between two ends of the housing 1, wherein the direction of the electric field is perpendicular to the direction along which the air is introduced into the housing; a ionization source 5 provided in the electric field region 4 to ionize the ionizable pollutants present in the air introduced from the inlet 2 to form the resultant ionized pollutants which will move to both ends of the housing 1 under the influence of the electric field; and a discharging device 6 for discharging the ionized pollutants that have arrived at the ends of the housing out of the filter device 100.

As shown in FIG. 1, the housing 1 in accordance with the present invention has a shape which is symmetrical with respect to a center line I. The high voltage electric field region 4 is symmetrical with respect to the center line I; the ionization source 5 is arranged along the center line I; and two sucking portions of the discharging device 6 are symmetrically arranged on opposite sides of the center line I. It is to be noted that FIG. 1 only shows a general and preferred design of the present invention, but is not intended to limit the present invention to the solution illustrated.

The air flows directly through the ionization source 5 via the air inlet 2 in the filter device 100. However, the filter device also comprises an air guiding element 7 for guiding the air to flow through the ionization source 5. The guiding element 7 can help the air flow through the ionization source 5, and prevent the air from flowing or diffusing directly into the interior of the housing 1 without passing through the ionization source 5.

The filter device 100 further comprises flow confining gratings 8 provided encompassing the ionization source 5. The shape of the gratings 8 is adapted to that of the ionization source 5, i.e. if the ionization source 5 has the shape of a cylinder, the gratings 8 in shape is also a cylinder. Additionally, the flow confining gratings 8 may be plate gratings provided on opposite sides of the ionization source 5 symmetrically. The flow confining gratings 8 is used to improve the filtration efficiency.

As shown in FIG. 1, the discharging device 6 comprises a pair of fans provided in the vicinity of the two ends of the housing, respectively, and discharging channels 9 arranged at an outer side of the pair of fans. Preferably, the pair of the fans is provided in the high electric field region 4. As an alternative, the discharging device is configured to include a pair of air pumps provided in the vicinity of the two ends of the housing. The filter device 100 also comprises a controller (not shown) to adjust the negative pressure in the housing 1 by controlling the discharging device 6. For example, the rotational speed of the fans or the air pumps may be adjusted so that the pressure of the housing 1 may be maintained within a predetermined range based on the pressure data detected by a pressure sensor (not shown) provided in the housing 1.

The ionization source can be the radioactive isotope $^{63}$Ni, namely a $^{63}$Ni radiation source, a corona discharge source, or a photo ionization source. In general, air is ionized under the effects of β-ray emitted by the radioactive isotope $^{63}$Ni directly or indirectly. Alternatively, a corona discharge source is used as a substitute for the $^{63}$Ni radiation source. The corona discharge source comprises two electrodes, across which an appropriate electric potential difference is applied so that a high voltage electric field is produced therebetween, thereby leading to the release of electrons from one electrode and their subsequent acceleration towards the other electrode. The released electrons with high energy will ionize the molecules in vapor phase encountered along their movement path. As an alternative, a photo ionization source can also be used instead of the $^{63}$Ni radiation source.

The present invention also relates to a filtering method for a filter device, wherein said filter device comprises a housing having an air inlet and a filtered air outlet, and said method includes the following steps:

(1) providing a high voltage electric field region between two ends of the housing, wherein the direction of the electric field is perpendicular to the direction along which the air is introduced into the housing;

(2) providing an ionization source in the high voltage electric field region;

(3) providing a discharging device for discharging the ionized pollutants which have moved to the ends of the housing out of the filter device; and (4) guiding the air to flow from the air inlet through the ionization source.

The present invention also relates to a filter device using the above-mentioned filtering method.

The operational principle of the filter device 100 in accordance with the present invention will be described below in detail by reference to FIG. 1. After the environmental air is introduced into the housing 1 of the filter device 100 via the air inlet 2, the air guiding element 7 guides the air to flow through the ionization source 5. During the process of flowing through the ionization source 5, the ionizable pollutants (i.e. nitro compound) present in the air are ionized to form molecule ion clusters by the ionization source 5 directly or indirectly, while the other components of the air which are not ionized will flow directly to the air outlet 3. Due to the fact that the ionization source 5 is disposed in the middle of the electric field, the molecule ion clusters will move away from the ionization source 5 or towards the two ends of the housing under the influence of the electric field, and then are discharged out of the housing 1 of the filter device 100 by the discharging device 6, i.e. fans, provided in the vicinity of the ends of the housing. With the use of the discharging device, the pollutants which have moved to the two ends of the housing can be prevented from diffusing back into the filter device. Therefore, the air flowing out of the air outlet 3 is clean air containing few ionizable pollutants.

It is to be noted, however, the filter device 100 is only effective to remove the ionizable pollutants present in the air instead of those pollutants which can not be ionized, that is, the filter device 100 in accordance with the present invention can only filter out ionizable pollutants. These ionizable pollutants, are exactly those interferents commonly encountered in applications using IMS based trace detectors, especially, in ion mobility technology.

It is to be noted that the electric field region 4 may be formed by a plurality of electrode plates 10 arranged symmetrically with respect to a center line I. Preferably, the electrode plates 10 further comprise two end electrode plates 10' disposed at the two ends of the electric field region 4. As shown in FIG. 1 for example, the fans 6 are disposed in a position between the ionization source 5 and the end electrode plates 10' which is in the vicinity of the end electrode plates 10'. Due to the presence of the end electrode plates 10', the ionized pollutants may flow through the fans under the influence of the electric field. Additionally, the end electrode plates 10' may be positioned in the vicinity of the discharging channel 9 of the housing 1.

Therefore, the present invention also provides a trace detector which can be used to detect substances based on ion mobility spectrometry, wherein the inlet port for the carrier gas of the detector is connected to the air outlet of the above-described filter device or filter devices using the above-described filtering method.

Although a few embodiments have been exemplified to describe the invention, it would be appreciated by those skilled in the art that changes and variants may be made in these embodiments without departing from the principles and spirit of the invention, the scope of which is defined in the claimed and their equivalents.

What is claimed is:

1. A filter device, comprising:

a housing, wherein the housing has an air inlet and a filtered air outlet, the housing has a center line extending through ends of the housing;

a high voltage electric field region provided between two ends of the housing, wherein the direction of the electric field being perpendicular to the direction along which the air is introduced into the housing, wherein the high volume electric field region is formed by a plurality of electrode plates arranged symmetrically with respect to the center line;

an ionization source provided in the electric field region to ionize the ionizable pollutants present in the air introduced from the air inlet to form the resultant ionized pollutants which will move towards both ends of the housing under the influence of the electric field; and a discharging device for discharging the ionized pollutants that have moved to the ends of the housing out of the filter device, the discharging device comprises a pair of fans provided in the vicinity of the two ends of the housing, respectively, and discharging channels provided at the outer side of said pair of the fans;

wherein the pair of fans is provided in the high voltage electric field region;

the electrode plates further comprise two end electrode plates adjacent to the discharging channels, each fan is disposed in a position between the ionization source and the end electrode plates which is in the vicinity of the end electrode plate.

2. The filter device as claimed in claim 1, further comprising:

an air guiding element for guiding the air to flow from the inlet through the ionization source.

3. The filter device as claimed in claim 2, further comprising:

flow confining gratings provided encompassing the ionization source.

4. The filter device as claimed in claim 1, further comprising:

a controller for adjusting the negative pressure in the housing by controlling the discharging device.

5. The filter device as claimed in claim 1, wherein the ionization source is a $^{63}Ni$ radiation source, a corona discharge source, or a photo ionization source.

6. A trace detector based on ion mobility spectrometry for the detection of trace amount of substances, wherein an inlet port for the carrier gas of the detector is connected to the air outlet of the filter device as claimed in claim 1.

7. A filtering method for a filter device, wherein said filter device comprises a housing having an air inlet and a filtered air outlet, the housing has a center line extending through ends of the housing, and said method includes the following steps:

providing a high voltage electric field region between two ends of the housing, wherein the direction of the electric field being perpendicular to the direction along which the air is introduced into the housing, wherein the high voltage electric region field is formed by a plurality of electrode plates arranged symmetrically with respect to the center line;

providing an ionization source in the high voltage electric field region;

providing a discharging device for discharging the ionized pollutants that have moved to the ends of the housing out of the filter device, the discharging device comprises a pair of fans provided in the vicinity of the two ends of the housing, respectively, and discharging channels provided at the outer side of said pair of the fans; and guiding the air to flow from the air inlet through the ionization source, wherein the pair of fans is provided in the high voltage electric field region;

the electrode plates further comprise two end electrode plates adjacent to the discharging channels, each fan is disposed in a position between the ionization source and the end electrode plate which is in the vicinity of the end electrode plate.

8. A trace detector based on ion mobility spectrometry for the detection of trace amount of substances, wherein an inlet port for the carrier gas of the detector is connected to the air outlet of filter devices using the filtering method as claimed in claim 7.

* * * * *